US006496736B1

(12) United States Patent
Carl et al.

(10) Patent No.: US 6,496,736 B1
(45) Date of Patent: *Dec. 17, 2002

(54) ENDOTHELIUM PRESERVING MICROWAVE TREATMENT FOR ATHEROSCLEROSIS

(75) Inventors: James R. Carl, Houston, TX (US); G. Dickey Arndt, Friendswood, TX (US); Patrick W. Fink, Fresno, TX (US); N. Reginald Beer, Houston, TX (US); Phillip D. Henry, Houston, TX (US); Antonio Pacifico, Houston, TX (US); George W. Raffoul, Houston, TX (US)

(73) Assignee: The United States of America as represented by the United States National Aeronatucis and Space Administration, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/500,538

(22) Filed: Feb. 9, 2000

Related U.S. Application Data

(60) Division of application No. 09/129,832, filed on Aug. 5, 1998, now Pat. No. 6,047,216, which is a continuation-in-part of application No. 08/641,045, filed on Apr. 17, 1996, now Pat. No. 5,904,709.

(51) Int. Cl.$^7$ .................................................. A61F 2/00

(52) U.S. Cl. ..................... 607/101; 128/898; 606/33; 606/42; 607/122; 607/156

(58) Field of Search ................................ 607/100–102, 607/115–116, 122–123, 154–156; 606/33–42, 45–50; 604/22; 128/898

(56) References Cited

U.S. PATENT DOCUMENTS

| 4,643,186 A | * | 2/1987 | Rosen et al. ................. 607/154 |
| 5,275,597 A | * | 1/1994 | Higgins et al. ................ 606/33 |
| 6,047,216 A | * | 4/2000 | Carl et al. .................... 607/101 |
| 6,233,086 B1 | * | 4/2001 | Carl et al. .................... 607/101 |

\* cited by examiner

Primary Examiner—Robert L. Nasser
(74) Attorney, Agent, or Firm—Hardie R. Barr

(57) ABSTRACT

Method and apparatus are provided to treat atherosclerosis wherein the artery is partially closed by dilating the artery while preserving the vital and sensitive endothelial layer thereof. Microwave energy having a frequency from 3 GHz to 300 GHz is propagated into the arterial wall to produce a desired temperature profile therein at tissue depths sufficient for thermally necrosing connective tissue and softening fatty and waxy plaque while limiting heating of surrounding tissues including the endothelial layer and/or other healthy tissue, organs, and blood. The heating period for raising the temperature a potentially desired amount, about 20° C. within the atherosclerotic lesion may be less than about one second. In one embodiment of the invention, a radically beveled waveguide antenna is used to deliver microwave energy at frequencies from 25 GHz or 30 GHz to about 300 GHz and is focused towards a particular radial sector of the artery. Because the atherosclerotic lesions are often asymmetrically disposed, directable or focussed heating preserves healthy sectors or the artery and applies energy to the asymmetrically positioned lesion faster than a non-directed bean. A computer simulation predicts isothermic temperature profiles for the given conditions and may be used in selecting power, pulse duration, beam width, and frequency of operation to maximize energy deposition and control heat rise within the atherosclerotic lesion without harming healthy tissues or the sensitive endothelium cells

11 Claims, 11 Drawing Sheets

ENDOTHELIUM PRESERVING MICROWAVE TREATMENT FOR ATHEROSCLEROSIS

This application is a division of application Ser. No. 09/129,832 filed Aug. 5, 1998, now U.S. Pat. No. 6,047,216, which is a continuation-in-part of presently copending U.S. patent application Ser. No. 08/641,045 entitled MICROWAVE TREATMENT FOR CARDIAC ARRHYTHMIAS, filed on Apr. 17, 1996, now U.S. Pat. No. 5,904,709.

ORIGIN OF THE INVENTION

The invention described herein was made in the performance of work under a NASA contract and is subject to the provisions of Section 305 of the National Aeronautics and Space Act of 1958. Public Law 85-568 (72 Stat. 435: 42 U.S.C. 2457).

BACKGROUND OF THE INVENTION

1. Field of the Invention

The present invention relates to methods and apparatus for using arterial blood pressure to dilate the lumen rather than expanding/cutting mechanical means so as to preserve the sensitive endothelial lining of the artery. More specifically, the present intention relates to production of a temperature profile within the arterial wall that corresponds to the atherosclerotic lesion size, shape, and position so as to necrose (ablate) connective tissue and soften plaque to thereby impart increased flexibility to the arterial

2. Description of Prior Art

Atheroscleroses, also known as hardening of the arteries, is one of the most common types of heart disease. Each year several hundred thousand people die of this disease or of complications relating thereto. By the age of forty, many people have already developed atherosclerotic lesions although no symptoms may appear. Atherosclerosis is a progressive disease wherein fatty, fibrous, calcific, or thrombotic deposits produce atheromatous plaques within the arterial walls as indicated generally in FIG. 11. Moreover, atherosclerosis tends to involve large and medium sized arteries such as the aorta, iliac, femoral, cerebral, as well as the coronary artery.

The atherosclerotic lesions are substantially comprised of plaque and scar tissue. The plaque is typically encapsulated within living connective tissue. Plaque is a heterogenous material, sometimes non-living, that may include calcified, wax-like. fibrotic, fatty, and brittle components. As the lesions within the arterial, walls grow in size, the lumen or passageway through the coronary artery may be correspondingly reduced in effective cross-sectional diameter (stenosis). The constricted (stenotic) lumen may then restrict the nutrient blood flow to muscles of the heart. Therefore, atheroscleroses is often a major contributing factor in both acute and chronic heart problems. Also, when the lumen is sufficiently narrowed, the rate of blood flow may be so diminished that an affixed blood clot (thrombus) or circulating blood clot (embolus) may spontaneously occur. Thus, the presence of atherosclerotic plaque not only reduces blood flow to the heart muscle but also is a major predisposing factor in coronary thrombosis.

While pharmacological treatment is often used to treat atherosclerosis, such treatment is sometimes considered to be insufficiently effective for increasing blood flow. Therefore, techniques such as balloon angioplasty (percutaneous transluminal coronary angioplasty) have been developed to mechanically increase the luminal opening.

However, mechanical techniques tend to traumatize the artery and often result in restenosis (reclosing of the lumen). Standard balloon angioplasty produces a gross trauma that severely injures the endothelium or lining of the artery. The endothelium is a very fragile layer of cells that performs the very important function of limiting thrombotic processes (See FIG. 12). Unlike other surfaces and materials, when blood cells come in contact with the endothelium there is no tendency to form a clot. The layer of endothelial cells normally covers the internal surface of all vessels, rendering the vessel surface compatible, i.e., non-thrombogenic and non-reactive with blood. If the endothelium is damaged, platelet deposition becomes a problem. Once this layer is injured, it does not normally row back uniformly and so damage thereof tends to permanently induce thrombotic processes. Injury to the endothelium has been associated with accelerating of atherosclerotic processes and/or restenosis.

At least one patent discussed hereinafter teaches to alleviate, at least to some extent, damage caused to the endothelium by providing a bioprotective layer around the angioplasty balloon to cushion, coat, and insert anti-inflammatory agents prior to opening the balloon. Another patent discussed hereinafter teaches reducing trauma damage to the endothelium by reducing angioplasty balloon pressure using heat and feedback control. However, due to the mechanical forces in balloon angioplasty, damage to the fragile endothelium may still occur. The bioprotective coatings may, according to the patent teachings, also reduce problems created by angioplasty-induced tissue tears or cleavages that can result in blood accumulation along the cleavage planes of arterial wall layers. The thickening caused during such problems may acutely block or occlude the arterial lumen and require emergency interventions such as stents or open heart surgery.

The trauma to the endothelium and to arterial walls from balloon angioplasty often evoke a potent inflammatory response, or restenosis (reclosing of the artery), whereby scar tissue growth and other processes occur to once again reduce the arterial lumen opening. As discussed in some detail below with respect to numerous different techniques, restenosis is probably one of the most significant problems that occurs with existing techniques for dilating or opening the arteries. Restenosis may occur due to numerous processes including the following: clots that crow gradually or contain growth hormones released by plateletes within the clot, clots formed due to exposure to collagen (connective tissue) which is highly thrombogenic, growth hormones released by other cells that cause smooth muscle cells and fibroblasts in the region to multiply, tears in the artery wall that expose blood to foreign material and proteins thereby producing clots, white cells that migrate to the area and lay down scar tissue, growth of new tissue due to any, kind of inflammatory response, and/or other factors that may cause the artery lumen to reclose. Several different processes may operate simultaneously to cause restenosis.

After balloon angioplasty procedures, narrowing of the artery by 50% may occur in more than one-half of the patients and about one quarter of the patients may require a repeat procedure by the end of one year. As mentioned above, restenosis (reclosing of the artery) remains a major problem in treatment of atherosclerosis by balloon angioplasty. While significant efforts have been made to dampen the reactive proliferation with a variety of pharmacological and genetic interventions, these interventions have thus far found limited or no successful clinical application.

Another problem with balloon angioplasty relates to the fact that the lesions, or atheromas, within arterial cross-sections are typically asymmetrically distributed. That is to say the lesions often occur on one side, portion, or sector of the artery while an opposite or adjacent sector of the artery is relatively free of the disease. It was initially postulated that the increase in endovascular pressure created with a balloon would somehow selectively crush lesions. However, given that the thick-walled sectors containing atheromas are typically abundant with dense collagen or connective tissue, the lesions may actually be less likely to undergo deformation than the opposite relatively thin-walled, lesion-free sectors. Thus, the maximum trauma produced by balloon angioplasty may well occur in the healthy sector of the artery. Some of the patents discussed hereinafter attempt to reduce, at least to some extent, this problem and related problems by first heating the artery to soften the plaque. However, unless the heating is applied selectively to the atheromas heat damage may occur to the artery and endothelium. As well, mechanical trauma may still occur to the endothelium and or other arterial components.

Acute closure of the lumen after balloon angioplasty remains the most common cause of failed angioplasty and occurs in approximately 5% of the patients. This complication may be associated with varying degrees of mortality that may exceed 50% when emergency coronary bypass surgery has to be performed.

For the above reasons, balloon angioplasty is often problematic due to restenosis or, less frequently, abrupt closure. Therefore, other catheter techniques for the mechanical widening of the lumen of diseased coronary arteries have been devised, including various tissue cutting techniques. Directional coronary atherectomy (DCA) involves the selective excision and retrieval of atheromatous or proliferative tissue obstructing the arterial lumen. In this procedure, the end of the catheter is provided with a fenestrated metal cylinder within which a piston-like cutter is moved via a torque cable. The cut tissue is recovered in a distal portion of the catheter. As compared with balloon angioplasty, the initial luminal widening achieved by DCA is similar or perhaps slightly better. Again, restenosis is problematical and, as before, the restenosis is probably acerbated by damage to the endothelium.

Rotational atherectomy incorporates a rotary file or burr (brass ellipsoid of vary in diameter covered with diamond chips—rotablator) into the distal portion of the catheter. The rotary file or burr is connected to a motor-operated drive shaft. Abrasion of the narrowed artery segments produces micro particles that are allowed to escape into the distal circulation for capillary entrapment. The rotablator has been used for treating heavily calcified lesions, lesions at branch points ('ostial disease'), and lesions involving long arterial segments ('diffuse disease'). Restenosis frequently occurs. However, because this instrument is often used to treat refractory or difficult-to-treat lesions, the results of the treatment are difficult to compare with those of balloon angioplasty. Transluminal extraction catheter atherectomy (TEC) involves use of a catheter with tip-mounted cutting blades. The tissue fragments are recovered by aspirating a flush solution during cutting. As with the other mechanical devices discussed above, restenoses are frequent.

In summary, the exact role of atherectomy or mechanical tissue cutting devices is not yet completely defined for treatment of atherosclerosis, but it is fair to say that such devices do not overcome the major complication of balloon angioplasty, i.e. restenosis.

Eximer (UV) laser coronary angioplasty systems are the only laser devices currently approved by the FDA for treatment of atherosclerosis. These devices act to remove tissue at the lesion from the artery. Light in the UV range can remove tissue by triggering photochemical reactions (photoablation). However, there is also considerable evidence that UV lasers remove tissue by a thermal mechanism like that of longer wavelengths (vaporization) such as visible, infrared, millimeter wave, and microwave spectra. One characteristic of eximer radiation (308 nm) is that the energy deposition is quite superficial. Accordingly, the procedure destroys the superficial cell layer (endothelial cells) and consequently produces a strong inflammatory response as does balloon angioplasty. Not unexpectedly, and in contrast to early claims. UV laser angioplasty does not have a lower restenosis rate than balloon angioplasty. This fact also suggests that tissue deformation, as occurs in balloon and rotablator procedures, is not the major determinant of restenosis because lasers do not forcefully distend artery walls.

Acute coronary closure after balloon angioplasty may be treated in several ways including perfusion balloon angioplasty (prolonged balloon inflation with protective distal coronary perfusion), atherectomy catheters as discussed above, and intracoronary stents. Coronary stents are designed to scaffold artery walls. The use of stents for acute closure is associated with a high initial success rate in maintaining arterial patency. However, stent therapy suffers from several drawbacks including subacute stent thrombosis, bleeding due to the necessarily aggressive anticoagulation treatment, and restenosis that occurs in 30% to 50% of the cases. The use of stents in non-emergency situations is an experimental procedure.

Another procedures for treating atherosclerosis is coronary artery bypass surgery. However, this procedure does not clearly suggest a better prognosis than balloon angioplasty and has the disadvantage of being a major surgical procedure.

Catheters with 1.2 or 1.7 mm ball tips for ultrasound (195 kHz) destruction of atheromatous lesions in artery walls have been reported.

Experimental use of microwave balloon angioplasty with a gap antenna operating at 2.45 GHz has been reported and the authors concluded that balloon angioplasty combined with microwave heating yielded wider luminal diameters four weeks after intervention. Other uses of heating in combination with balloon angioplasty are discussed in the following patents.

U.S. Pat. No. 4,583,556, issued Apr. 22, 1986, to Hines et al., discloses a microwave applicator with a suggested use for treating cancer. The microwave applicator is said to provide uniform heating without hot spots and includes a first electrical conductor and a second electrical conductor substantially shielding the first conductor in a transmission line configuration. A coil is provided as a third electrical conductor that surrounds an unshielded portion of the first conductor. No particular microwave frequencies are designated.

U.S. Pat. No. 5,496,311, issued Mar. 5, 1996, to Abele et al., discloses an expandable balloon catheter that simultaneously heats the plaque and applies pressure to tissue of the lumen with feedback and software control to thereby significantly reduce the balloon pressure necessary to dilate the artery. The heating is preferably $I^2R$ (convective) to about 50° C. to 70° C. at the balloon surface, for about 15 to 60 seconds, with balloon pressure of about 2 atm. The patent teaches that avoiding the high stress of normal balloon angioplasty (about 10 atm balloon pressure) reduces side effects such as post operation platelet deposition, clotting, intimal proliferation (scarring) and hormonal changes that cause restenosis. Abele et al. teach that high balloon stress may also cause long term problems including aneurysms (weakening or thinning of the vessel wall). Thermal and/or reduced mechanical injure to the endothelium may well occur with this technique. No mention is made of directing heat towards a particular segment of the artery.

U.S. Pat. No. 5,470,352, issued Nov. 28, 1995, to C. M. Rappaport, discloses a balloon angioplasty device that includes a microwave antenna preferably operating at about 1.8 GHz. The goal of the antenna design is to heat plaque to temperatures in the range of 95° C. to 143° C. without overheating healthy artery tissue by providing heating power in a circumferentially oriented electric field. However, the somewhat erroneous presumption is made that plaque is necessarily on the inside of the artery walls rather than normally being within the artery walls where the circumferential field will still apparently heat healthy tissue. As seen above, the applied temperature is quite high. Furthermore, there appears to be no suggestion to direct helical antenna radiation towards a particular radial segment of the artery.

U.S. Pat. No. 5,370,677, issued Dec. 6, 1994, to Rudie et al. discloses a transurethral substantially helical microwave antenna catheter operating at about 915 MHz for thermal treatment of benign prostatic hyperplasmia (BPH). Directional application of heat is accomplished in the range of 45° C. to 60° C. by placing the antenna offset from the axis of the shaft. The heating process takes a period of about 45 minutes. to necrose or ablate, tumorous prostate tissue while a catheter water cooling jacket keeps temperatures adjacent the catheter below about 45° C. to protect adjacent healthy tissue such as the urethra, ejaculatory duct and rectum. The necrosed tissue is reabsorbed by the body. Dilation of a coronary artery is not disclosed.

U.S. Pat. No. 5,359,996, issued Nov. 1, 1994, to L. L. Hood, discloses an ultrasonic cutting tip assembly for an ultrasonic cutting instrument having an ultrasonic transducer.

U.S. Pat. No. 5,199,951, issued Apr. 6, 1993, to J. R. Spears, discloses a balloon angioplasty method for treating a lesion in an arterial wall by bonding a bioprotective material thereon with temperatures in the range of 80° C. to 100° C. for about twenty seconds with another twenty second wait before the balloon is deflated. The bioprotective coating is used to coat the endothelium while it is repairing itself after balloon angioplasty as well as provide drug carriers for the artery to alleviate problems of restenosis and thrombus. U.S. Pat. No. 5,109,859, issued May 5, 1992, to R. D. Jenkins, discloses a laser ablation catheter system guided by ultrasound sonography to remove atherosclerotic plaque from coronary arteries.

U.S. Pat. No. 5,057,106. issued Oct. 15, 1991, to Kasevich et al., discloses a balloon angioplasty microwave catheter system used for heating arterial plaque. The patent teaches that heating of the plaque reduces restenosis and that the plaque should preferably be heated to about 100° C. for about 30 seconds using a 10 GHz microwave source.

U.S. Pat. No. 4,927,413, issued May 22, 1990, to R. Hess, discloses a flexible shaft for use with balloon angioplasty.

U.S. Pat. No. 4,881,543, issued Nov. 21, 1989, to Trembly et al. discloses a microwave applicator for heating stroma at 2.45 GHz to effect shaping of the cornea with apparatus for cooling of the cornea to protect the endothelium by flow of saline transverse to the antenna axis.

U.S. Pat. No. 4,808,164, issued Feb. 5, 1989, to R. Hess, discloses a catheter for balloon angioplasty that includes a flexible shaft defining a hollow passage.

U.S. Pat. No. 4,700,716, issued Oct. 20, 1987, to Kasevich et al. discloses a microwave antenna for treatment of tumors or other materials by hyperthermia with temperatures of about 50° C. induced with microwave frequency in the range of 500 MHz to 5 GHz. There does not appear to be any provision for protecting endothelial cells from damage.

U.S. Pat. No. 4,685,458, issued Aug. 11, 1987, to M. E. Leckrone, discloses a catheter for use in removing undesired material from a duct with a patients's body including a cutting element, an inflatable bladder, and a pair of abutments to surround the material being removed so that the material is vacuumed out through the catheter.

U.S. Pat. No. 4,643,186, issued Feb. 17, 1987, to Rosen et al. discloses a balloon angioplasty catheter with microwave antenna to heat and soften the plaque by radiation and heat convection. No particular frequencies are provided and no particular precaution is, provided for the endothelium.

U.S. Pat. No. 5,129,396, issued Jul. 14, 1992, to Rosen et al., discloses a balloon angioplasty catheter with microwave antenna to measure balloon distension.

U.S. Pat. No. 4,576,177, issued Mar. 18, 1986, to W. W. Webster, Jr., discloses an optical fiber for transmitting laser radiation and an ultrasonic transducer mounted at the tip of the catheter for transmitting and receiving ultrasonic signals.

U.S. Pat. No. 5,150,717, issued Sep. 29, 1992, to Rosen et al., discloses an angioplasty catheter that includes a coaxial transmission line with an elongated center conductor and outer conductor. The transmission frequency is preferably about 3 GHz.

U.S. Pat. No. 4,998,932, issued Mar. 12, 1991. to Rosen et al. discloses a chip generator for either laser or RF radiation located on the distal end of the catheter.

U.S. Pat. No. 5,607,419, issued Mar. 4, 1997, to Amplatz et al., discloses a catheter to apply UV light to a blood vessel after balloon angioplasty. The patent teaches that this treatment retards growth of smooth muscle cells.

I.E.E.E. Transactions on Biomedical Engineering. Vol. BME-34 No. 2. February 1987, by D. M. Sullivan, D. T. Borup, and O. M. P. Gandhi, entitled "Use of Finite Difference Time-Domain Method in Calculating EMI Absorption in Human Tissues" describes the FDTD method as applied to bioelectromagnetic problems and demonstrates a 3-D scan of the human torso.

I.E.E.E. Transactions on Biomedical Engineering,. Volume 35, No. 4. April 1988. by D. Andreuccetti, M. Bini, A. Ignesti, R. Olmi, N. Rubino, and R. Vanni, entitled "Vee and Polyacrylamide as a Tissue Equivalent Material in the Microwave Range", discloses the use of polyacrylamide gel to simulate biological tissues at microwave frequencies.

Other related references include Critical Reviews in Biomedical Engineering, by K. R. Foster and H. P. Schwan. Volume 17. Issue 1, 1989, entitled "Dielectric Properties of Tissues and Biological Materials" and the book "Field Computation by Moment Methods", by R. F. Harrington, MacMillan Press, 1968.

A review of the above references reveals that a long felt need exists for apparatus and methods to dilate the lumen of the artery without injuring endothelial cells so as to avoid the long term problems often associated with trauma thereto. If the atherosclerotic lesions are radially external of the intima, e.g., in the media, then the intimal layer including the endothelium should be preserved from injury. At a bare minimum, the energy for softening fatty deposits should be radially directed toward the segment or arc of the artery in which the atherosclerotic lesion is located, if the lesion is asymmetrically located within the arterial wall, to greatly reduce the likelihood of damage to healthy tissue. Healthy tissue in the adventitial layer should be preserved. A temperature profile should be controlled to produce heat in a region corresponding to the size and position of the atherosclerotic lesion. The heating should preferably be effected very quickly to avoid extended blockage of the artery with the catheter. Those skilled in the art have long sought and will appreciate the present invention that provides solutions to these and other problems.

SUMMARY OF THE INVENTION

The present invention provides methods and apparatus for thermally necrosing (ablating) connective tissue and softening plaque within atherosclerotic lesions while controlling the temperature rise in other arterial tissues and in the endothelial layer of the artery. By means of the present invention, the time required to raise the temperature of an atherosclerotic lesion by a sufficient level (about 20° C.) is usually less than one second. The lesion is heated while limiting damage to other tissues. The microwave power level of operation and frequency is chosen so that a temperature increase from absorption of microwave energy in the endothelium is limited by the blood exchange rate to a desired safe temperature range. The frequency of operation and other factors affect the depth at which energy is deposited. Heat conduction effects are related to the time period of operation.

As used herein unless otherwise stated, ablation or necrosis refers generally to creating a temperature profile in the biological tissue that results in a cessation of biological functioning of the remaining living or diseased cells in the tissue, such as connective tissue, that is part of the plaque in the artery wall. For instance, thermal ablation or necrosis refers to heating cells by about 20° C. to the general range of roughly 57° C. (which temperature may vary and is often dependent on the heating duration) to cause them to cease biological functioning. Once ablated or necrosed, any connective cell tissues within and/or encapsulating the plaque will no longer mechanically support the arterial wall. The absence of mechanical support by the connective tissue induces the lumen in the region or sector of the atheroma to be more flexible in response to the arterial pressure, and especially the elevated arterial pressure at the restriction. Without connective tissue, flesh has the approximate tensile strength of Jello®. However, care must be taken that healthy arterial smooth muscles are not also damaged to the extent that aneurysms are likely to form. Excessive heating of healthy tissue could result in dilation that escalates because greater arterial surface area results in a larger force that may then cause increased dilation, and so on. According to the present invention it is not necessary or desirable to vaporize or char cells for ablation purposes because overheating may cause undesirable side effects. The heating profile is conservatively controlled where possible within time constraints to limit overextending the artery so as to induce aneurysms in the long term. Therefore, the procedure may be performed in stages to attempt to avoid such effects. The temperature profile size and shape may be predicted by computer simulation and effected by microwave radiation having controllable characteristics including frequency, antenna power, pulse width (heating time), and beam width.

For this purpose, a method is given for thermally heating an atherosclerotic lesion in an artery to treat atherosclerosis while preserving an endothelial layer of the artery. A catheter is provided that has a microwave radiator at one end thereof.

A frequency of operation for the microwave radiator is provided within a frequency range of from about 3 Gigahertz to about 300 Gigahertz. A microwave power level of operation, pulse duration of operation, and frequency of operation is used such that a heat rise from energy deposition in the endothelial layer is limited by a blood flow rate and a specific heat of the blood to within a selected temperature rise less than an amount that will damage the endothelial layer.

The frequency is selected so that a profile of the heat rise due to energy deposition is maximum within in the atherosclerotic lesion as compared to tissues and fluid surrounding the atherosclerotic lesion.

Typically, a pulse duration of operation of less than two seconds is required for necrosing living tissue within the atherosclerotic lesion. In many cases, the pulse duration will be less than one second or less than one-half second. The microwave radiation is directed at a radial segment of the artery in which the atherosclerotic lesion is substantially positioned, because, typically, the lesions are asymmetrically disposed around the arterial lumen. It is undesirable to apply heat to the remaining healthy tissue opposite or adjacent the lesion. Therefore, a radially directable energy source is provided for use in directing microwaves towards the particular sector of the artery wherein the lesion is located. In one preferred embodiment wherein a waveguide antenna is used, the frequency of operation is in the range of 30 GHz to 300 GHz. The waveguide antenna is preferably a radically beveled open ended waveguide antenna. In another embodiment, frequency in the range of 3 GHz to 300 GHz is generated using a chip positioned on a distal portion of the catheter. Presently available MMIC chips cover a range of 50 to 110 GHz with more power per chip being available at the lower end of the spectrum. To achieve greater than one watt of power, it may be necessary to sequentially connect two or more of the chips together to increase radiation power from the catheter. Preferably, microstrips are used to connect the chips, if necessary, to thereby prevent increasing the diameter of the catheter.

The transcatheter method of dilating the artery includes steps such as positioning the catheter within the artery adjacent to the atherosclerotic lesion, radiating the atherosclerotic lesion with sufficient energy to raise the temperature thereof, and controlling temperature in the endothelial layer to a temperature that does not injure the endothelial layer by limiting total energy deposited in the endothelial with respect to heat lost due to conduction and convection of fluid flow through the artery. After sufficient energy is deposited in the atherosclerotic lesion to necrose living tissue therein and increase flexibility thereof, the natural arterial pressure is used or allowed to dilate the artery. By radiating the energy toward a radial segment of the arterial wall in which the atherosclerotic lesion is positioned, the radiated energy deposited outside of the radial segment of the arterial wall in which the atherosclerotic lesion is positioned is greatly reduced or eliminated. While the connective tissues are necrosed, the plaque that includes wax and fatty deposits is also softened thereby further increasing flexibility of the artery.

A temperature profile for deposition of the energy within the wall of the artery may be predicted using a computer program. The program simulates transcatheter microwave antenna temperature control within an arterial all having an atherosclerotic lesion therein. Although it may be desirable to start with information about the position of the lesion, characteristics thereof and so forth, and obtain operation periods. frequencies and so forth, it is also possible to provide such information to determine the temperature profile. Thus, a frequency of operation from 3 GHz to 300 GHz, the power input, heating time, and antenna beam width may be input to achieve the desired temperature profile. Generally, the program will determine heat energy transferred by heat conduction within a plurality of layers and determine heat energy removed by fluid flow through the artery. For visual ease, it will normally be desirable to plot at least one cross-section of temperature profile in the arterial wall. If the atherosclerotic lesion is asymmetrically disposed within the artery, it is necessary or at least highly desirable to determine the radial section in which the atherosclerotic lesion is located. The size of the atherosclerotic lesion may be an input to the program. The program will model characteristics of the atherosclerotic lesion using a plurality of computer cells of a small size which can simulate the characteristics of a material within the atherosclerotic lesion being provided for each of the computer cells, e.g. electrical permittility and conductivity at the frequency of operation and thermal conduction properties. Because the lesions are heterogeneous, such values may vary for each of the plurality of computer cells.

The energy added to computer cells) that represent portions of the simulated arterial wall, is determined by energy entering and leaving the computer cells. The isothermic profile is determined for a particular time period preferably within a desired time period range of less than five seconds. The profile at any time will vary significantly due to heat conduction and energy deposited. The isothermic profile varies significantly for any particular frequency within a desired frequency range of from 3 GHz to 300 GHz.

The microwave waveguide embodiment of the invention is preferably used with a catheter comprising a microwave transmission line having first and second opposing ends wherein the first end is adapted for connection to a microwave power source having a frequency of operation between about 25 or 30 GHz to about 300 GHz. At least a portion of the microwave transmission line should be operable as a microwave waveguide such that the microwave waveguide has an outer conductor defining an inner region filled with homogenous dielectric material. The microwave radiator is then disposed at the second end of the microwave transmission line. The microwave radiator preferably comprises an open ended waveguide antenna having a beveled portion of the outer conductor of the antenna. The beveled portion is beveled with a selected angle so that energy is directed radially from the open ended waveguide antenna. Dielectric material disposed at the beveled portion preferably extends towards a termination end of the antenna. In one embodiment the inner region is filled with dielectric material that forms an axial extension that extends beyond the beveled portion so as to be operable for exposure to the artery. The microwave transmission line may include a coaxial portion having an inner and outer conductor and a transition portion between the coaxial portion and the microwave waveguide. Continuous microwave radiation is preferably limited to less than five seconds and, generally much less. In another embodiment, a monopole antenna is provided and, more specifically, includes a double disk loaded monopole antenna.

It is an object of the present invention to provide an improved method for dilating an artery without harming the endothelial layer or healthy tissues.

It is a further object of the present invention to provide a technique for conveniently predicting isothermic region sizes and shapes from power inputs, antennas. frequencies of operation, time duration for heating, and other relevant factors that affect the transfer of heat energy.

Yet another object is to limit restenosis by limiting damage to the artery during a procedure for opening the artery.

Yet another object is to take advantage of new tools that describe the lesions more clearly so that treatment can be tailored in response to information about the particular situation.

Yet another object of the present invention is to provide a test device that allows a close approximation of the actual physical structures within the body by which the various devices and heating factors can be tested in a realistic setting for purposes such as verifying predicted results as to heating, gathering data, refining techniques, and the like.

A feature of the present invention is a transcatheter heating instrument that includes presently preferred embodiments for a microwave radiator.

Another feature of the present invention is a range of frequencies of operation shown to be especially useful for supplying energy to atherosclerotic lesions.

Another feature of the present invention is a simulation for determining microwave radiation and the resulting temperature effects in the blood/tissue/plaque environment due to the heterogeneous nature of this environment including the atherosclerotic lesion. An advantage of the present invention is the wide range of factors that can be adjusted to consider prediction of future results.

Another advantage of the present invention is the ability to refine techniques both before actual construction and after actual construction of the particular devices to be used.

Another advantage of the present invention is that long term problems associated with damage to tissues such as endothelial cells from the procedure is limited.

Yet another advantage of the present invention is the ability to tailor and otherwise refine apparatus and/or techniques to the requirements of a particular application.

These and other objects features and advantages of the present invention will become apparent from the drawings, the descriptions given herein, and the appended claims.

While the present invention will be described in connection with presently preferred embodiments, it will be understood that it is not intended to limit the invention to those embodiments. On the contrary it is intended to cover all alternatives, modifications, and equivalents included within the spirit of the invention and as defined in the appended claims.

DESCRIPTION OF PREFERRED EMBODIMENTS

The techniques of the present invention are designed to treat atherosclerosis without damaging the important endothelial layer. Once the catheter is positioned, the heating of the atherosclerotic lesion takes little time, in some cases less than one-half second. The power levels are low—in the range of about 1 watt. The catheter is designed to operate while blood continues to flow through the artery. A temperature profile is produced in the arterial wall that necroses or ablates connective tissue, softens waxes and fats, and allows the arterial pressure to more gently act to dilate the artery. Frequency of the radiation has a significant affect on the depth of maximum energy deposition. The beam width can be selected to be in accord with the size of the lesion. Where the lesion(s) are asymmetrically disposed in a specific arc of the arterial wall. the energy is directed toward the arc and the angle of focus for the radiator can be adjusted accordingly. This provides much more efficient use of the energy, making the procedure quicker. It also protects the remainder of the healthy tissue from being overheated. Therefore radiation is preferably more specifically tailored to concentrate energy within the atherosclerotic lesion based on the position and depth thereof, as well as the size and shape of the lesion. As more improved information becomes available by ever improving technology about the more precise structure of the lesion, such as with MRI and CAT scans, the information can be used to further refine predictions when computing temperature profiles through the computerized modeling techniques disclosed, as discussed further in regard to the computer simulation program. Furthermore, the test assembly of the parent of this application may be used to quite realistically test the instrument using damaged arterial segments so that extensive experience and training can be obtained prior to use.

Figure 11:
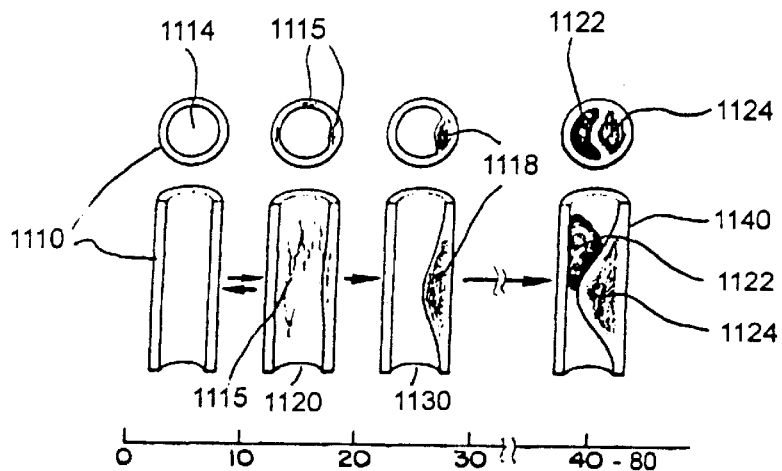
FIG. 11 is a diagram representing a typical progression of atherosclerosis leading to a complicate lesion that ulcerated and developed thrombosis.

As a general background. FIG. 11 discloses the progressive nature of atherosclerosis with a variable time line in terms of age. Artery 1110 is initially free of lesions or fatty tissue so that lumen 1114 is completely open. Between very roughly the age of 15 to 30, fatty streaks 1115 begin to develop as shown by artery 1120. These fatty streaks may disappear as indicated by the double arrows between artery 1110 and 1120. Thus, the body has the ability to reabsorb fatty streaks, to some extent. Over age 30. waxy and fibrous tissue or atheroma 1118 forms as indicated in artery 1130. The atheroma 1118, or atherosclerotic lesion, shown in artery 1130. is in the uncomplicated state, or non-thrombotic state, that leaves some lumen, however narrow. The waxy, and especially the fibrous tissue does not normally disappear as frequently as did fatty streaks 1115. Without assistance of some type, the body has less ability to reabsorb such tissue. At some time, very roughly in the age range of 40 to 80, a complicated lesion 1124, with plaque that typically also includes calcification, as indicated in artery 1140 may occur, The body tends to have little ability to reabsorb the calcification although some pharmacological treatments exist wherein the coal is to assist the body to effect reabsorption of calcified plaque. Complicated lesion 1124 is considered complicated because it may be hemorrhaged, ulcered, calcified, or thrombogenic, and may produce a heart attack, or myocardial infarction, due to blockage of blood flow. In this case. thrombus or blood clot 1122 has formed to block artery 1140.

Therefore, as the disease slowly progresses, trauma to the endothelial layer may occur that results in a complication. For instance, if blood is then exposed to collagen tissue that typically encapsulates the plaque, and/or for the numerous other reasons discussed hereinabove, blood clot such as thrombus 1122 may develop that closes the artery lumen and results in a heart attack due to the heart muscle not receiving sufficient. or any, blood flow. Obviously, it is preferable that treatment begin prior to the complicated or occlusive stage of artery 1140. Such treatment may be directed to slowing down the atherosclerotic processes involved and may involve dieting, monitored exercising, lowering cholesterol, decreasing blood pressure, and the like. If the lumen needs to be dilated to obtain sufficient blood flow to the heart muscles, and pharmacological means are unable to provide suitable relief, means as discussed hereinafter may be used to dilate the lumen while attempting to maintain the important healthy aspects of the artery. It will be observed that often, as shown, atherosclerotic lesions are asymmetrical, as indicated in artery 110. In accord with the present invention, the healthy tissue not affected by atherosclerosis should be protected and not ad be placed under stress. Any healthy tissues that are damaged in the process of dilating the lumen may become involved in processes of restenosis wherein a relatively rapid reclosure of the artery may occur within one year or so after the dilation procedure.

According to the present invention, plaque is preferably heated so as to soften and melt it. After heating, the plaque volume or volume of the lesion may be somewhat reduced and some plaque components, such as the fatty elements, may perhaps be reabsorbed to a certain decree. The heating also necroses or ablates connective tissue so that the arterial lumen can dilate due to natural arterial pressure. Without the aid of connective tissue, flesh loses connective strength and may be similar to a paste or gel in overall tensile strength. Care also needs to be taken to not ablate too much tissue surrounding the artery. If the artery has insufficient strength, it may become subject to problems of aneurysms. As noted previously, the possibility of aneurysms can also be a long term problem associated with balloon angioplasty treatment. Apparently, simply opening the diameter of the lumen is not, in itself, necessarily the cause of restenosis. By avoiding damage to healthy tissue including the endothelium, it is expected that this technique will alleviate some, and perhaps many, of the processes of restenosis.

However, it will be recognized that essentially dilation procedures are simply delay procedures that permit improved blood circulation while, hopefully, the underlying causes of the atherosclerosis, which may be many causes, are alleviated. However, because restenosis tends to proceed at a much faster pace than the underlying problem of atherosclerosis, restenosis remains a very significant barrier to successful long term treatment of atherosclerosis. It is therefore a basic goal of the present invention to alleviate problems of restenosis while dilating the artery.

Figure 12:
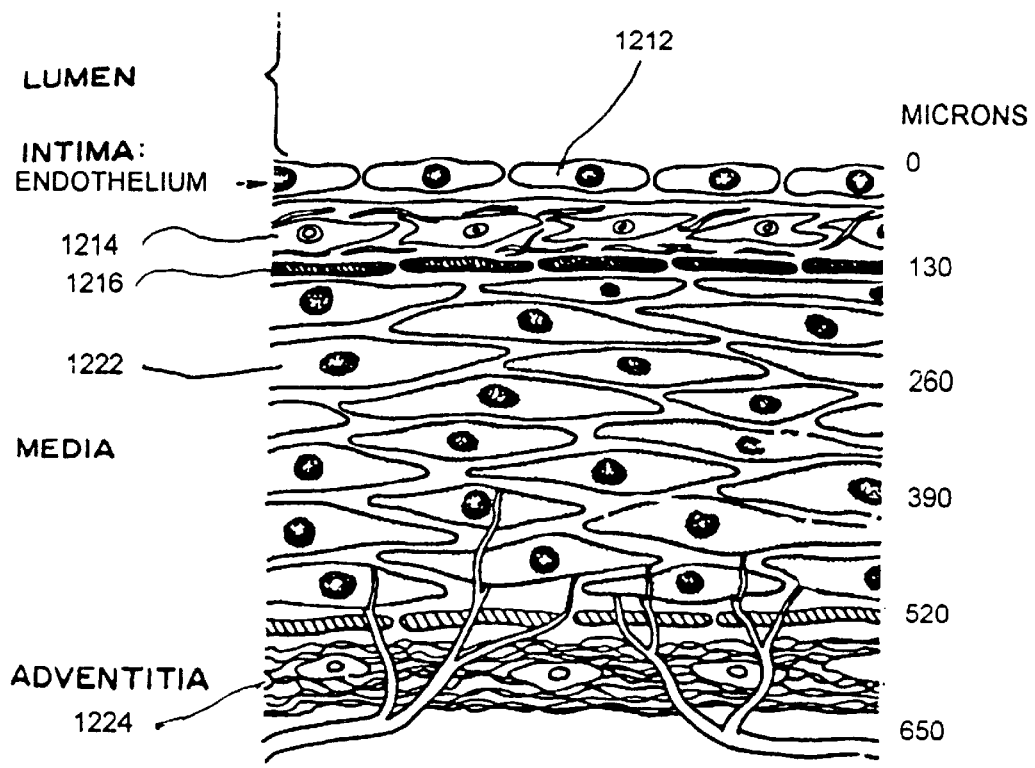
FIG. 12 is a diagram that relates to the general structure of the arterial wall including the endothelium and intimal layer, media, and adventitia.

FIG. 12 discloses the general, make up of a healthy arterial vessel wall in greater detail disclosing the cellular layers of tissues and provides, very approximately, the width in microns of the cellular layers in an average healthy vessel wall. The values of the width of the vessel wall may change significantly for a vessel wall having an atherosclerotic lesion in it. Plaque tends to somehow make its way into and to build up within the intimal and/or medial layers, apparently due to numerous processes that may underlie the atherosclerosis. The intimal layer includes the endothelium layer wherein endothelial cell 1212 is indicated and an additional layer of cellular tissue 1214. As discussed previously, blood does not clot when in contact with the endothelial layer but has a tendency to do so when it comes into contact with many other types of tissues such as those found within plaque, e.g., collagen or connective tissue. Such tissues are highly thrombotic. Protection of the endothelial layer is therefore very important and, if it remains healthy, will probably aid in preventing or slowing of numerous of the processes of restenosis, as well as the processes involved in atherosclerosis. Internal elastic membrane 1216 separates the intimal layer from medial layer that includes smooth muscle cells 1222. Adventitial layer 1224 provides for lymph drainage and blood flow within the arterial wall. The lumen is located adjacent intimal layer and defined by the endothelium, in the health artery. Atherosclerotic lesions are found within the vessel wall, generally in the intimal or medial layers. It is desirable to apply heat to the lesion without traumatizing the surrounding, tissues, including the endothelium and adventitial layers. Where possible, it is desirable to protect the healthy intimal layer and/or medial layers when the lesion has not formed therein. Therefore, a system is necessary for developing a controllable temperature profile that maximizes heat within the lesion and wherein the temperature drops off quickly outside the lesion to avoid damage to healthy tissue.

Figure 1:
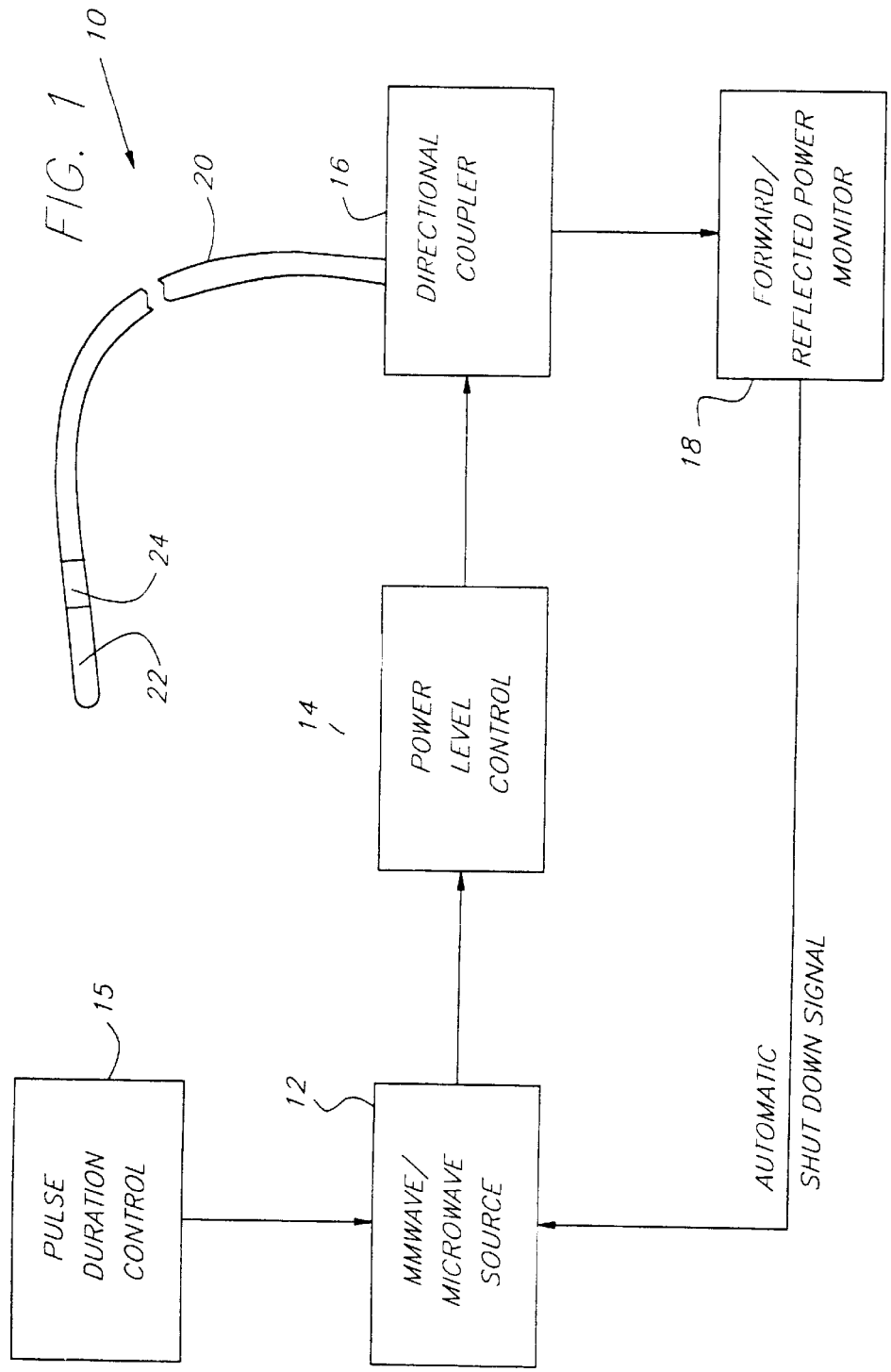
FIG. 1 is a block diagram showing a system for treating atherosclerosis.

Referring now to FIG. 1, the major components of system 10 disclose a preferred embodiment of the present invention for treating atherosclerosis. Generally, system 10 includes a millimeter wave/microwave power source, a catheter transmission line in the form of a waveguide, coaxial cable or combination of the two, and an antenna/radiator located at the end of the catheter. Another type of catheter without a microwave transmission line is also shown as an alternative embodiment in FIG. 10 and is discussed hereinafter.

Power source 12 is capable of producing up to 10 watts at a controlled power level. However, generally the power required may be considerably less if the atherosclerotic lesion is asymmetrically oriented and depending on the size thereof. It is presently anticipated that heating will generally be sufficiently effected at levels closer to about one watt, depending on the volume of the lesion. The subsequently shown test results are normally based on an antenna power of one watt or less. Power level control 14 is used to adjust the antenna power to the desired level. Power source 12 supplies power at the desired frequency, which as shown hereinafter, can be used to control the temperature profile. Selected frequencies for the present invention, depending on the application as discussed hereinafter, are in a range from 2 GHz to 300 GHz. It is presently anticipated that a separate power source would preferably be used or required for each frequency selected.

Pulse duration control 15 provides a pulse that controls the time that antenna power is applied. In the present embodiment, pulse duration control 15 is arranged to be pulsed with a desired pulse duration of from 0.1 to 10 seconds, with the accuracy of the pulse duration controlled within 2%. As will be seen subsequently, the pulse duration was less than about 0.5 seconds during the tests for anticipated volumes of lesion size which were for asymmetrically spaced atheromas. As discussed subsequently, the necessary power can be applied more quickly, or efficiently, if the asymmetrical nature of the typical atherosclerotic lesion is taken into consideration. Not only is heating time reduced thereby limiting treatment time to a desirable minimum, but also healthy tissue is spared. The pulse duration may be increased or decreased as necessary and precision of the pulse length could be narrowed, if desired although the small 2% variation in pulse duration is not anticipated to significantly affect the thermal profile produced.

Directional coupler 16 is used to match impedances for more efficient application of power to the antenna. Forward/reflected power monitor 18 detects if a mismatch has occurred such that power is not being radiated from the antenna with sufficient efficiency. In that case, power will not be radiated efficiently and therefore power source 12 may be shut down automatically.

Catheter 20 provides a means of directing energy from power source 12 to antenna 22. At the higher range of frequencies from approximately 25–30 GHz to 300 GHz, it is likely that a flexible waveguide would provide the most efficient means of power delivery. At the lower frequencies, from approximately 2 GHz to 25–30 GHz, a coaxial cable will probably be preferable for efficiency of power delivery. In some cases, it may be desirable to have a coaxial cable for a portion of catheter 20 formed of coaxial cable and a portion formed of waveguide. If that proves to be desirable as may occur for flexibility purposes, cost, convenience or other reasons, then an impedance matching transition member, such as transition member 24, may be used to connect between the coaxial cable portion and the waveguide portion. In yet another embodiment, such as that discussed in the embodiment of FIG. 10, it may be preferable to locate the millimeter wave source directly behind the antenna, thereby reducing transmission line losses.

Figure 2:
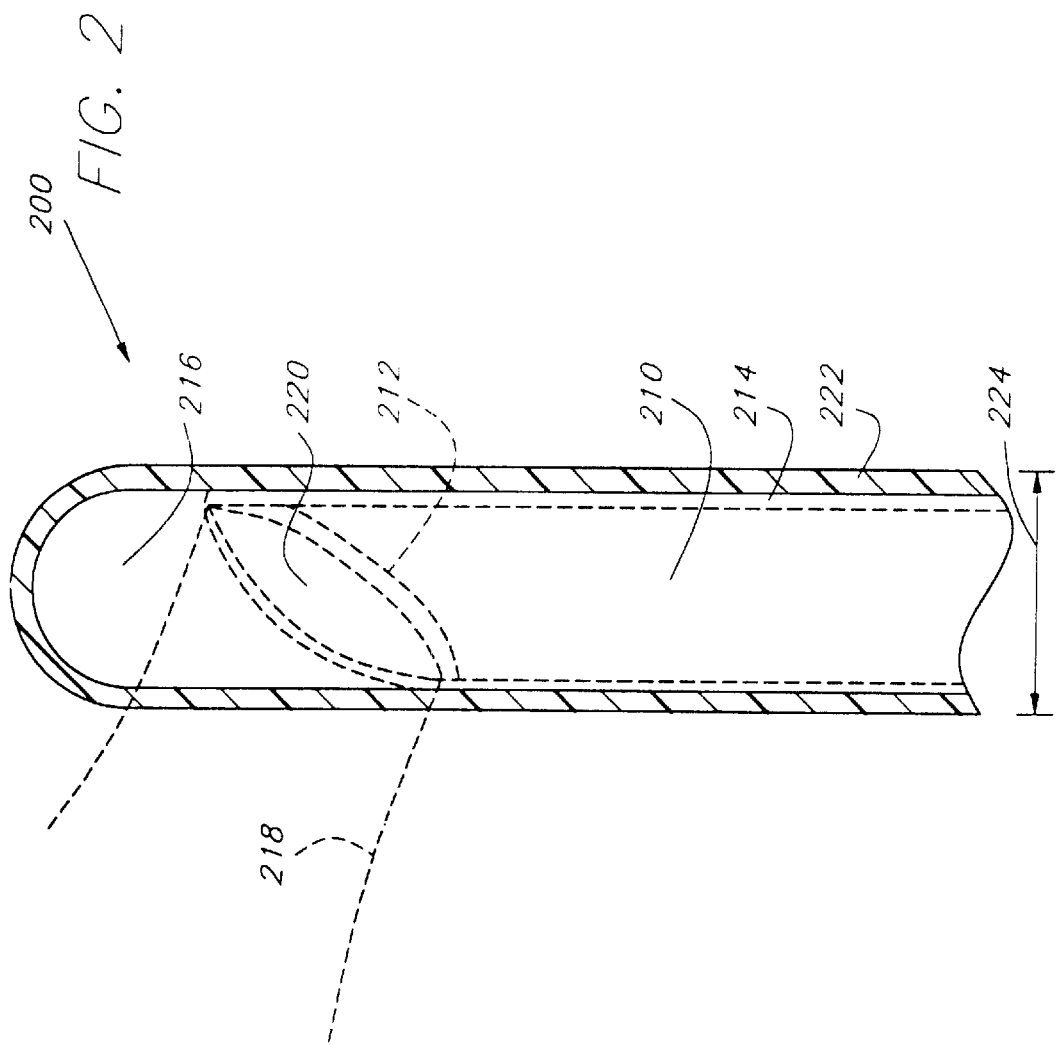
FIG. 2 is an elevational view partially in section, showing a radically beveled circular wave guide antenna.
Figure 3:
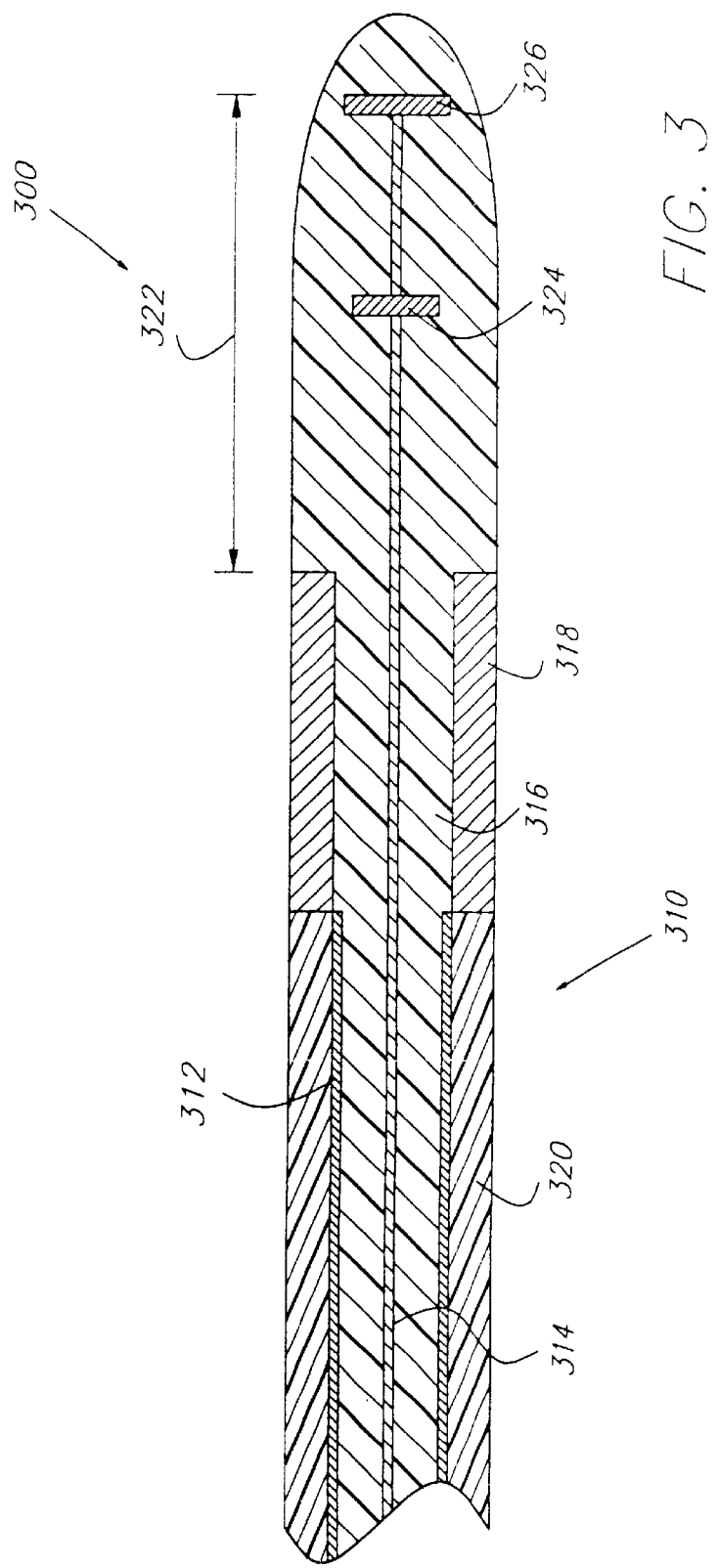
FIG. 3 is an elevational view, in section, showing a double disk loaded monopole antenna.

Antenna design is also preferably made dependent of the selected frequency of operation. For operation in the higher range of frequencies, the presently preferred embodiment of the invention would use a radically beveled open ended waveguide antenna, as shown in FIG. 2, and discussed hereinafter. The radically beveled antenna produces a radiation beam that is directed to a selected arc of the lumen. For frequencies at the lower end of the frequency range, disk loaded monopole antennas, as shown in FIG. 3, have proven to be effective. Disk loaded monopole antennas are discussed in some detail in the parent to this application, which application is incorporated by reference herein. At the low end of the frequency range, antennas tend to radiate much more broadly. Therefore, such antennas may be more suitable when the cross-sectional distribution of lesion(s) is of the type sometimes referred to as a circumferential lesion that yield a central lumen completely surrounded by a circumferentially distributed lesion.

More commonly, an eccentric atheroma is found that yields an eccentric lumen. For this reason, the radically beveled open ended antenna that operates in the higher range of frequencies may be preferable. For this and other reasons discussed hereinafter, a choice of 95 GHz was made for the initial test program in which selected arteries, in vitro, will be heated via a transcatheter antenna. It will be noted that the eccentric lumen may be subdivided further into categories including a slitlike or circular lumen with the circular lumen being positioned eccentrically within the cross-section of the artery. There are numerous variations in between, depending largely on the size of the arc of the lesion. The slitlike lumen may have a lengthwise diameter almost as wide and the original lumen. Therefore. adjustment of the beamwidth of the antenna may be used, as discussed subsequently, or some additional rotation of the antenna may be used, to heat the desired portion or all of the atheroma.

FIG. 2 discloses a presently preferred radiator for the higher frequency range of from about 25–30 GHz to 300 GHz in the form of a radically beveled circular waveguide antenna 200. Waveguide material 210 is preferably a low loss ceramic material that is suitably flexible for use in a catheter. The waveguide antenna and waveguide preferably have a diameter 224 of about two millimeters and is circular. Metallic sheath 214 is cut and removed to provide for a radical bevel 212. Metallic sheath 214 conforms and surrounds waveguide material 210. The angle of bevel 212 affects the width of the directional beam 218, indicated in dash, produced by antenna 200 so that a smaller angle with respect to the longitudinal axis of the antenna produces a wider beam. A minimum and maximum angle may be used depending on variables related to the losses at beveled interface 220. As indicated, directional beam 218 is directed radially outwardly from beveled interface 220. As discussed hereinafter in regards to the computational simulation, beam 218, depending on the type of antenna, may be a focused beam, a spreading beam in one direction, or a spherically spreading beam. The beam of the waveguide antenna may be a focussed beam without significant spreading although, for illustrative purposes only, some spreading is indicated as may be possible to produce depending on the angled cut of the bevel. A selected beamwidth with appropriate spreading tendencies is desirable and necessarily depends on the size and location of the lesion in the wall.

Tip 216 may be formed of waveguide material 210 and preferably extends past radical bevel 212 in metallic circular cross-sectioned sheath 214. Tip 216 may also be formed of a different dielectric material selected for loading purposes. However, construction of antenna 200 may be simplified somewhat if the same waveguide material 210 is used. A medically acceptable nonthrombogenic material is used to form sheath 222 of the catheter. Federal regulations presently require use of a new catheter for each procedure rather than allowing sterilization and reuse of the same catheters. This factor may make it possible to provide for variations in the catheters and the catheter antennas to match the particular usage of size and shape of the lesion without any substantial increase in cost.

FIG. 3 discloses a double disk loaded monopole antenna 300 in accord with the present invention. The general construction features of such an antenna are covered in some detail in the parent of this application so that only the basic features are covered herein. Antenna 300 is essentially simply a smaller antenna than the antenna disclosed in the parent, and reference is made to the earlier patent that is incorporated herein by reference. Antenna 300 is connected to coaxial cable portion 310. Coaxial cable 310 comprises an outer metallic conductor 312 and a centrally located conductor 314. Insulator material such as TEFLON® or other suitable material forms the core 316 of coaxial cable 310 and also preferably extends into antenna 300. To limit current flow along the catheter, metal choke 318 is employed. Insulative jacket 320 is provided on the catheter but is cut off at the beginning of metal choke 318 so that radiation may occur. mainly from the discontinuities of antenna 300 starting at the beginning of gap 322. Gap 322 is related to the frequency of operation. The second and third discontinuities include tuning disk 324 and disk 326. Tuning disk 324 may be used to adjust the center frequency of operation of the antenna so as to flatten the response over the bandwidth of operation, which tends to be fairly broad. Antenna 300 is preferably used for lower frequencies such as the range from 2 GHz to 25 or 30 GHz radiation proceeds outwardly in all directions from antenna 300 and therefore antenna 300 is preferably used for treatment of circumferentially disposed atherosclerotic lesions.

Figure 4:
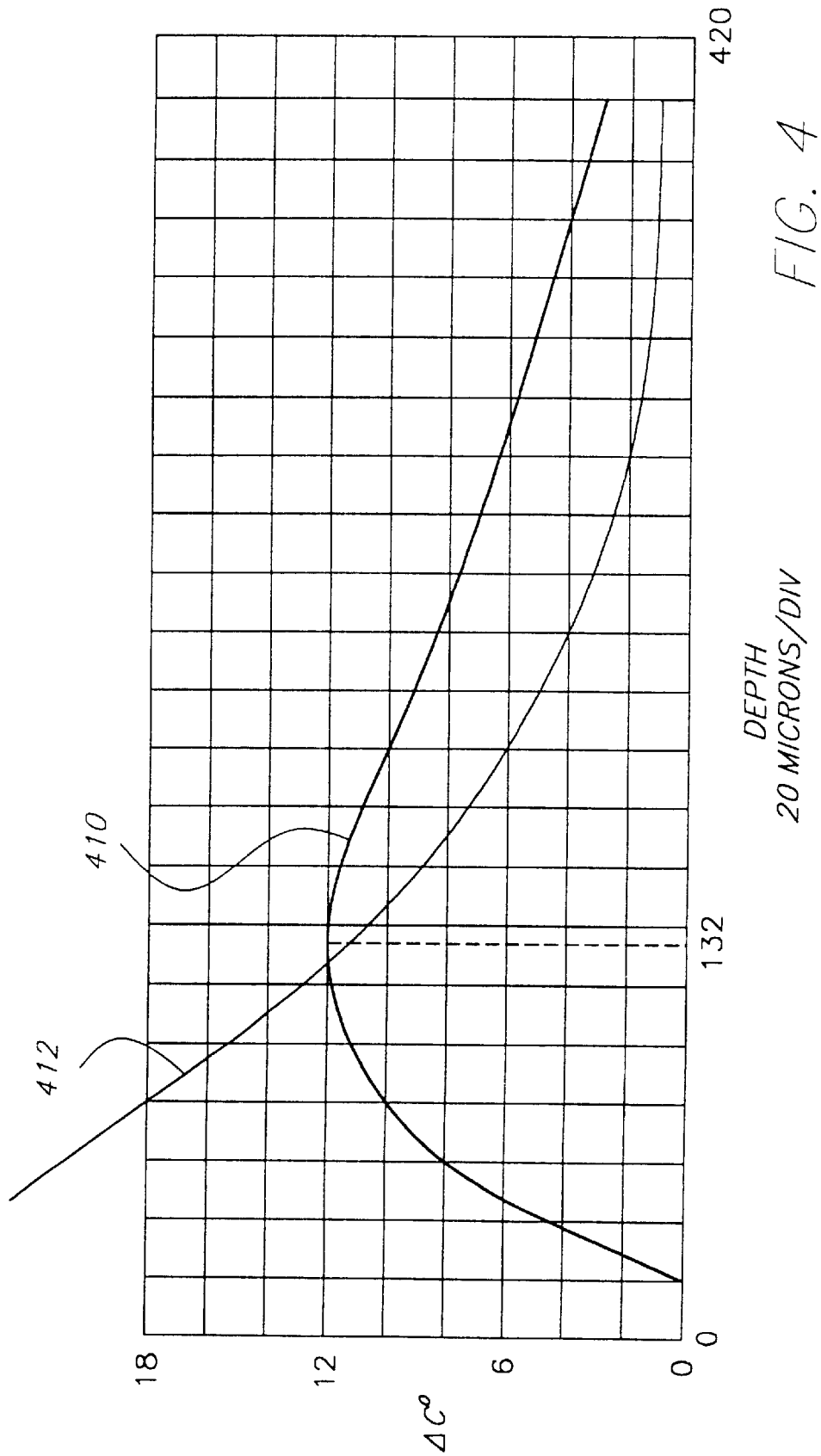
FIG. 4 is a graph of temperature to tissue depth showing the temperature equilibrium and percentage of energy deposited though 400 microns of 5 cubic millimeters of muscle tissue for a 0.5 second pulse duration with one watt antenna power and a frequency of 95 GHz.

Referring to FIG. 4, in operation, at frequencies above 40 GHz, most energy is deposited within the atherosclerotic lesion and little energy will pass into and beyond the adventitial layer because of rapid decay of the electromagnetic wave. The frequency used in the chart of FIG. 4 is 95 GHz. The maximum temperature rise for the example of FIG. 4 occurs at about 132 microns as indicated by heavy line 410 which represents the temperature profile as a function of depth. The heating time is 0.5 seconds and the volume heated is 5 cubic millimeters. The antenna power is 1 watt. A focused beam is used and the maximum temperature increase is approximately 12 degrees for the example of FIG. 4. The material used for testing is beef heart muscle. Keeping all variables the same except frequency, the maximum temperature rise for the situation of FIG. 5 occurs at 246 microns, therefore indicating the significant effect that changing only frequency has on the temperature profile.

For a focused beam antenna, power absorption decreases as $\exp(-2\alpha\ r)$ where $\alpha$ is the attenuation constant, and r is the distance from the antenna. This exponential decay is indicated by the thin line 412 in FIG. 4 that indicates the relative deposition rate of energy as a percentage. For a very broadly radiating antenna, power absorption decays as $\exp(-2\alpha\ r)/r^2$. The decay is more rapid because of spherical beam spreading resulting in the $r^2$ term in the denominator. Therefore, when a broad beam radiator is used for radiating an asymmetrically disposed lesion, only a portion of the radiated energy is used so that generally only a portion of the lesion is illuminated. The extraneous energy is wasted or produces heating of non-diseased tissue or proximal blood. Except for circumferentially diffused lesions, a focused beam is therefore preferred.

Figure 5:
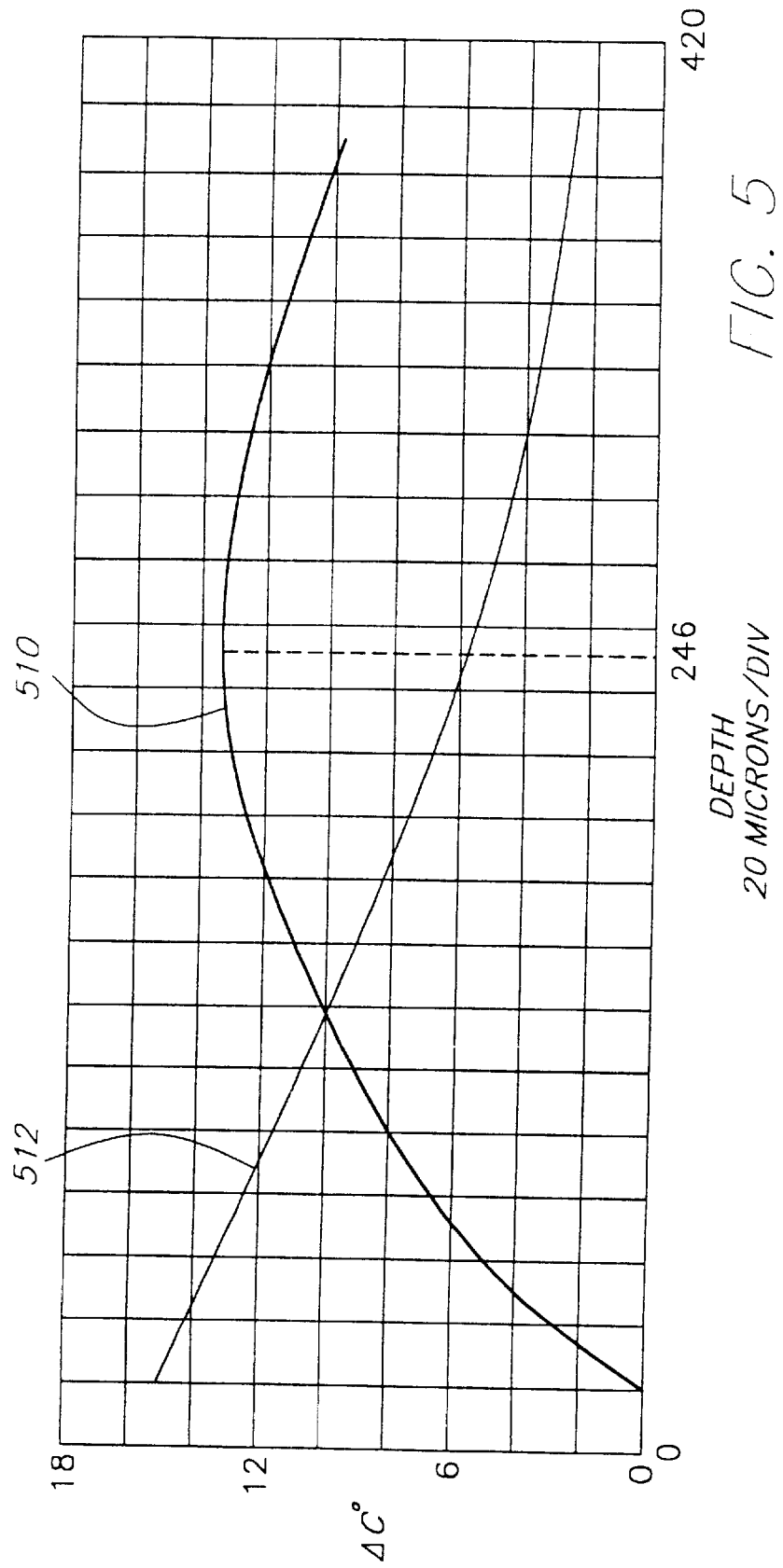
FIG. 5 is a graph with variables being essentially the same as those of FIG. 4, except for a frequency of operation of 40 GHz.

In addition to electromagnetic heat deposition, thermal conduction plays a critical role in obtaining the desired temperature profile within the arterial wall. At any depth within the wall, thermal equilibrium is reached when the heat gained by electromagnetic deposition is equal to the heat lost by the heat loss mechanisms. At the internal surface of the artery, i.e., the endothelial layer, heat lost by conduction and convection to the flowing blood as well as heat lost by conduction to the outer layer of the transcatheter antenna, will prevent any significant temperature rise. As indicated in FIG. 4, heat rise for the first 20 microns is zero. The maximum heat rise over the endothelial layer, of approximately 30 microns, is only about 2 degrees centigrade. At shallow depths within the intimal layer, temperatures are depressed by strong thermal conduction to the blood due to the relatively short distance thereto. At deeper depths, temperatures rise until a depth of maximum temperature is reached. In the chart of FIG. 4, the maximum temperature is reached at 132 microns from the surface of the vessel. By adjusting the frequency, beam width, pulse time, and power, the maximum temperature can be placed at the center of the atherosclerotic lesion. At depths beyond the lesion, temperatures drop because electromagnetic deposition, as indicated by thin line 412, is significantly diminished. Therefore, in the example of FIG. 4, the adventitial layer and much of the muscle tissue of the medial layer is well preserved. In the example of FIG. 5, where all the controlled variables are the same, i.e. power delivered, pulse duration, and antenna bandwidth, the maximum temperature occurs at 246 microns as indicated by temperature profile thick line 510, which is typically well beyond the intima and into the media where many lesions occur. Thin curve 512 discloses a more flattened energy deposition curve. In both cases, the important endothelial layer is well preserved.

Temperature profiles can be customized to the size, shape, and type of the lesion. The controllable factors that determine the temperature profile are the following: (1) antenna power delivered. (2) pulse length, (3) frequency, and (4) antenna design/beamwidth control. A computer program simulation has been written that calculates the three dimensional isothermal contours for a given frequency, power level, pulse duration, antenna type, tissue complex permittivity and tissue constants. Examples are shown in the isothermal type printouts of FIG. 6–FIG. 8. It will be noted that the program can be used with heterogenous tissues that are typical with atherosclerotic lesions, although in the present examples the tissue is assumed to be homogenous. It is anticipated that testing with actual atherosclerotic tissue in the test unit will refine the values used. e.g., for thermal conductivity and conductivity. As well, test information about the particular situation available or that may become available in the future due to advances such as refined SARI photos may be of value in refining the data for particular cases.

Figure 6:
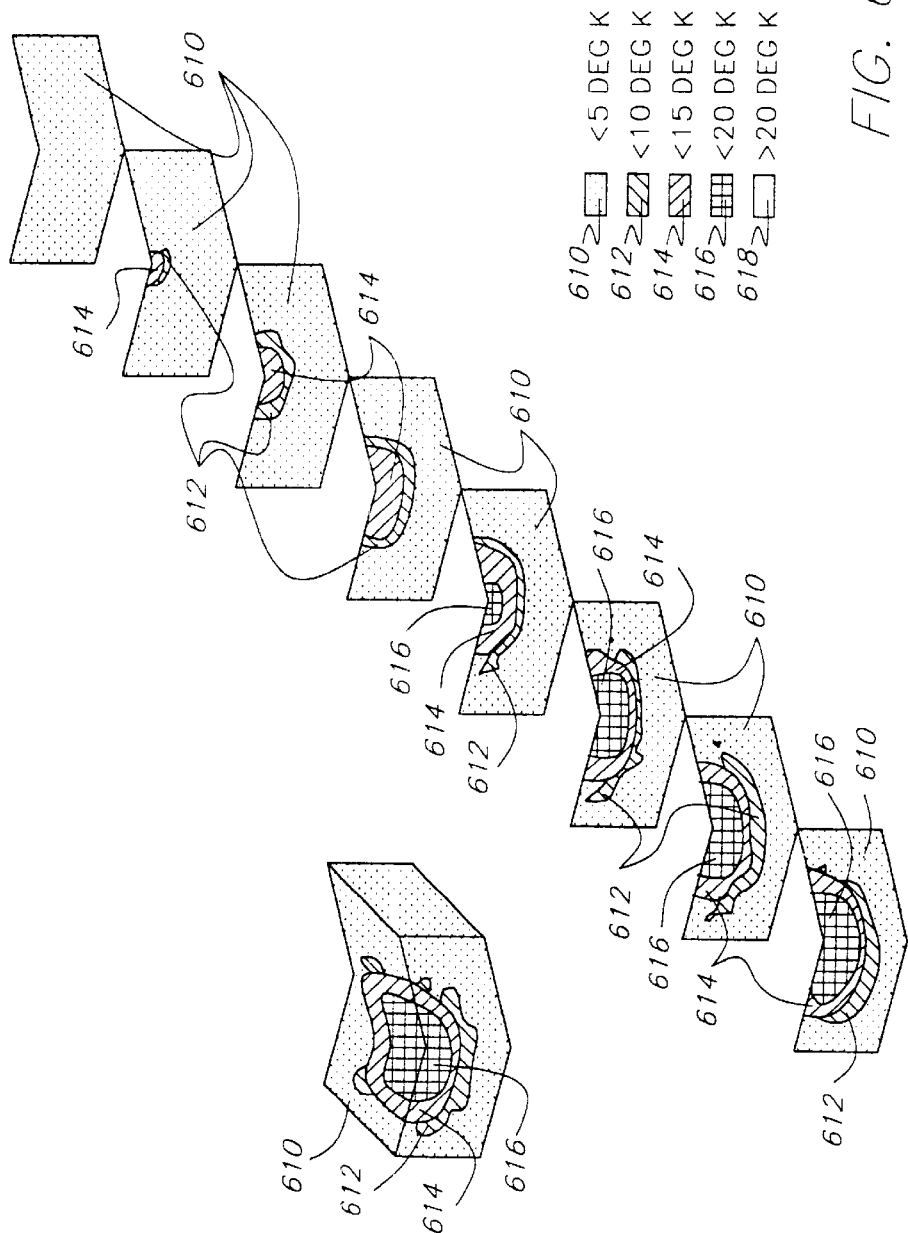
FIG. 6 is a schematical representation of an isothermal temperature profile produced in 1.68 mm$^3$ of myocardium tissue in 0.299 seconds of heating as a function of distance along an antenna at 95 GHz.
Figure 7:
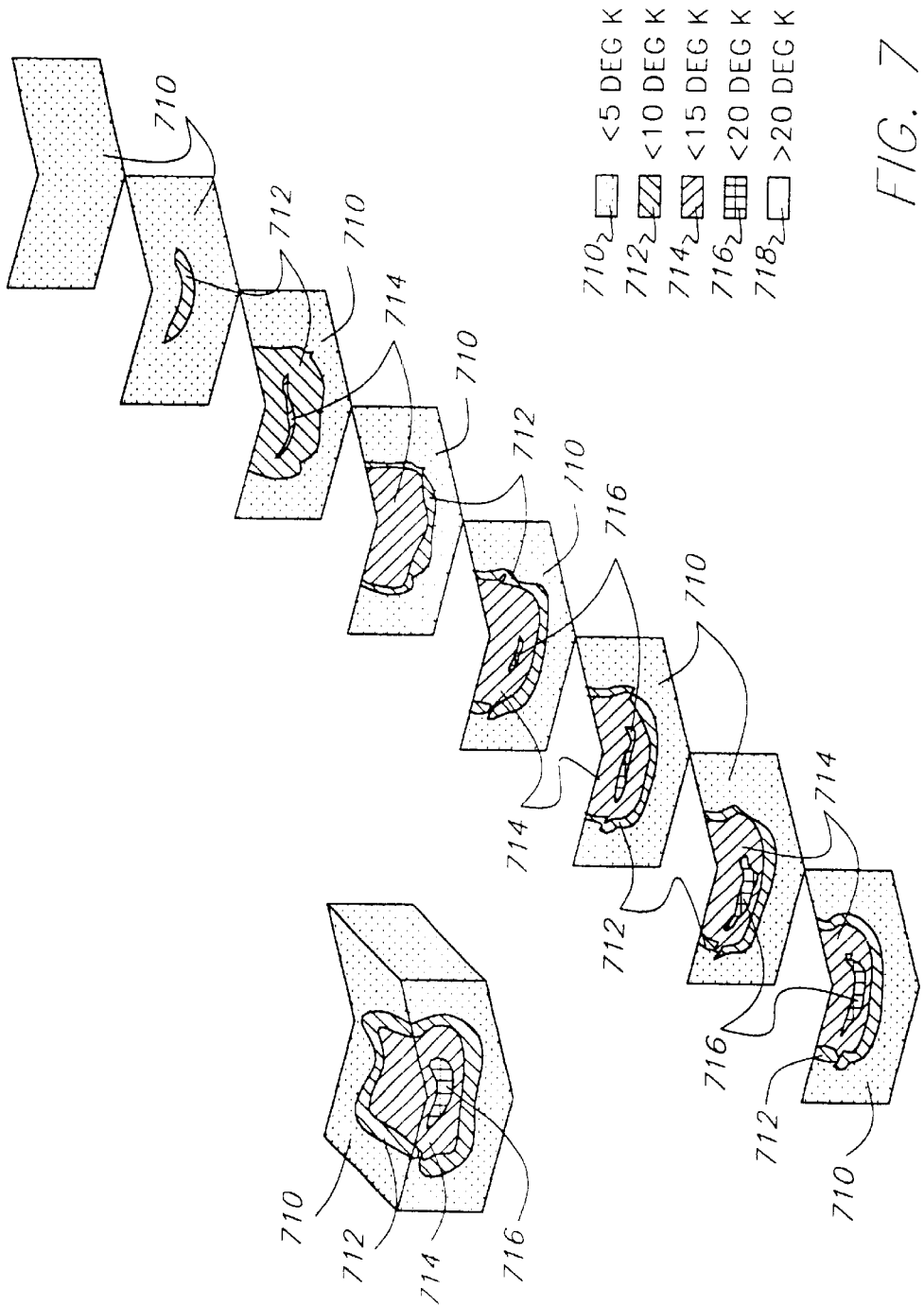
FIG. 7 is a schematical representation of an isothermal temperature profile having substantially the same variables with the frequency being 40 GHz.
Figure 8:
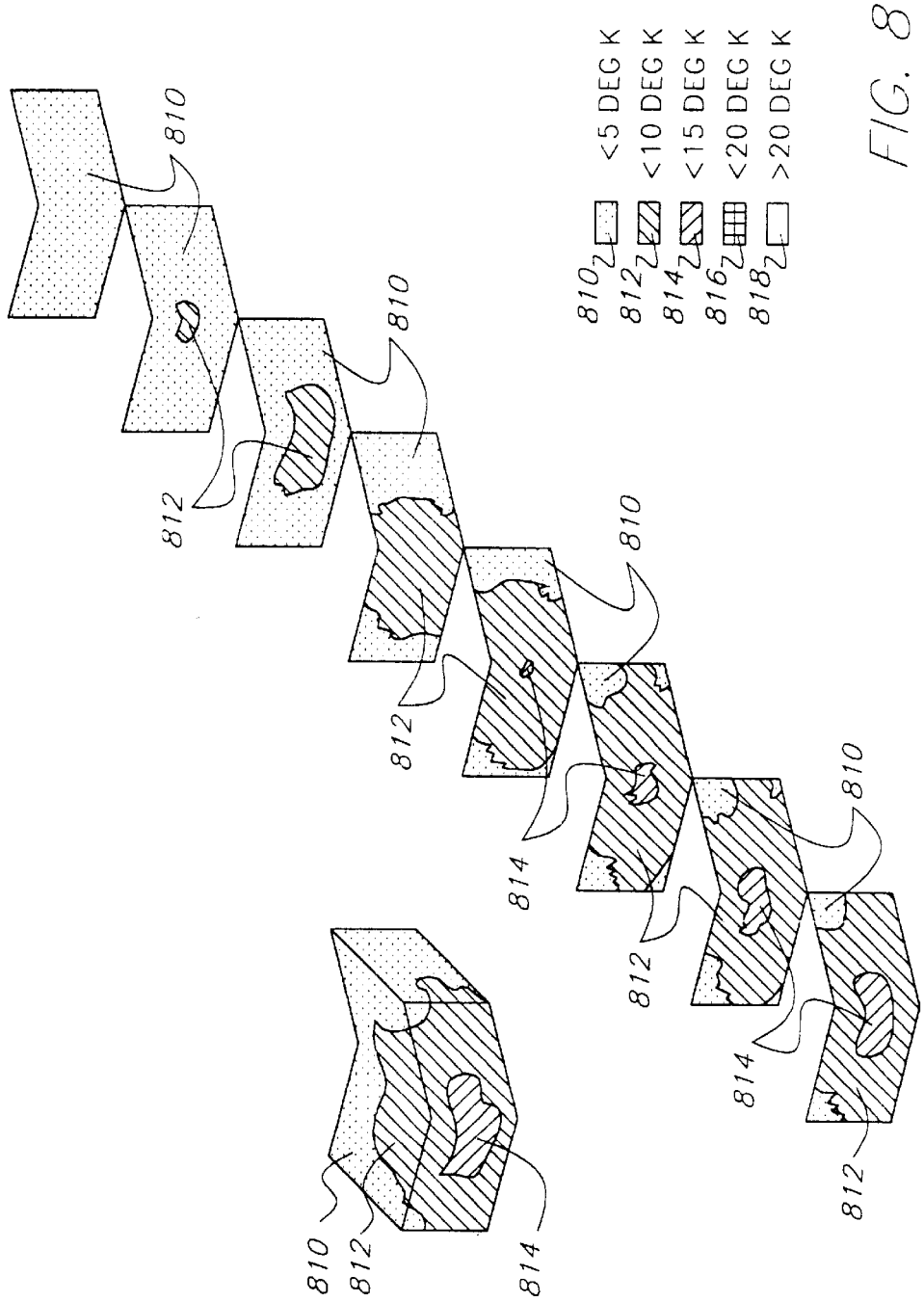
FIG. 8 is a schematical representation of an isothermal temperature profile having substantially the same variables with the frequency being 15 GHz.

In FIGS. 6, 7, and 8 all variables are kept constant except frequency, although the isothermal regions viewed in FIG. 8 are twice as large. The type of printout shown is a sectionalized isothermal profile although other types of printouts could be used or different views could be projected. These particular views are shown for example only. In FIG. 6, the computer simulation uses a frequency of 95 GHz. In FIG. 7, the selected frequency is 40 GHz and in FIG. 8, the selected frequency is 15 GHz. The large plot on the left in each figure shows the heating of a cube of myocardium with half of the cube cut away in the z direction to show the isothermal profiles in the x-y plane. The eight individual cross-sections shown on the right are artificially expanded in the direction so that the isothermal profiles in the x-y plane can be observed.

It will be seen that the results from the computer simulation are similar to that shown in the physical testing as per the charts of FIG. 4 and FIG. 5. An increase in frequency, keeping all other variables constant, tends to move the center of the position of maximum temperature closer to the antenna. This is seen by reviewing regions 616, 716, and 816 that of the respective FIGS. 6, 7, and 8 that indicate regions having, temperature increases between 15 and 20 degrees Kelvin. The regions of relatively moderate increases, i.e. 612, 712, and 812 for temperature increases between 5 and 10 degrees Kelvin. and 614, 714, and 814 for temperature increases between 10 and 15 show a somewhat similar shift in the same direction. The coolest regions are those of 610, 710, and 810 that reflect regions having a temperature increase less than 5 degrees Kelvin.

Figure 9:
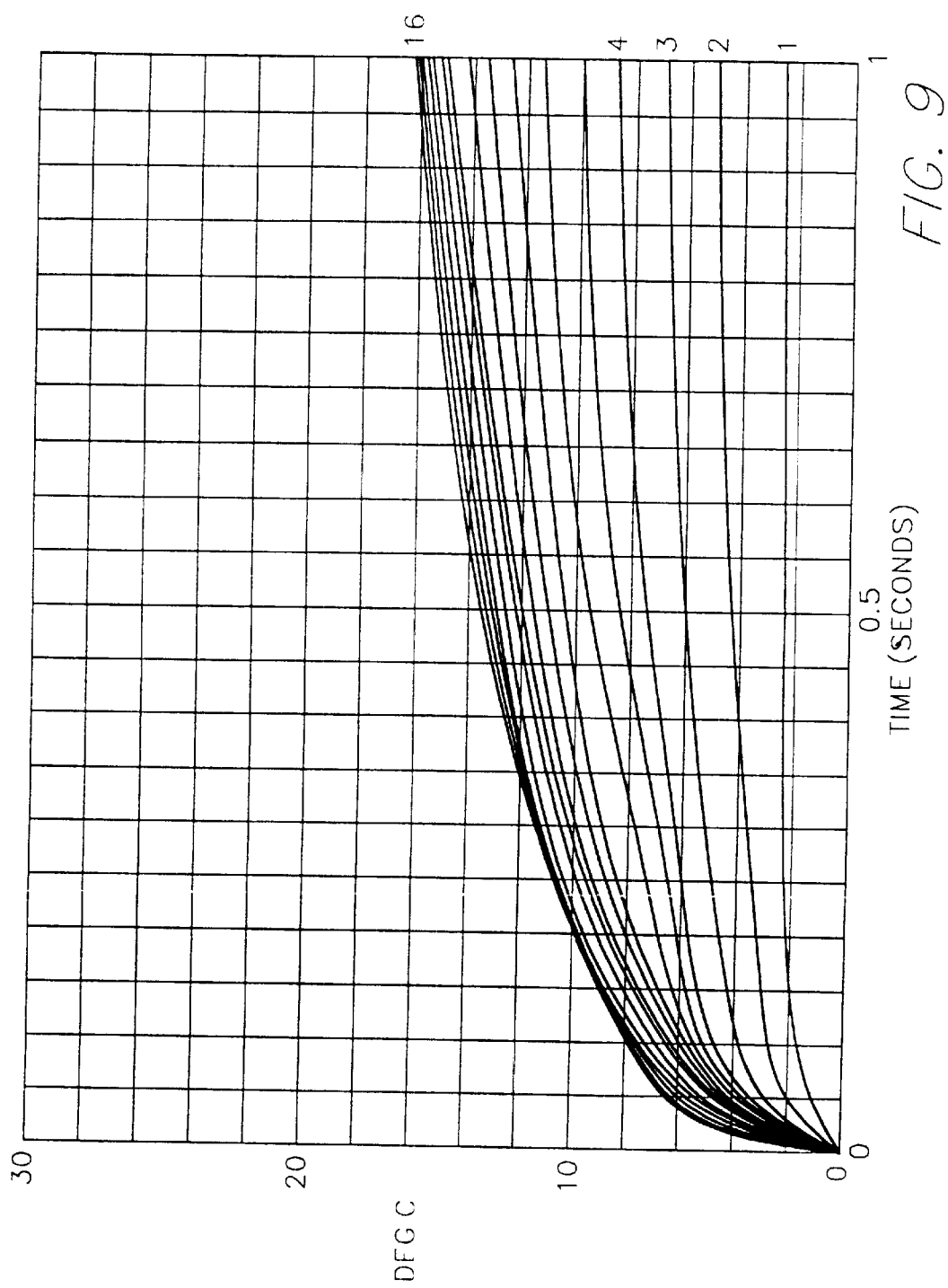
FIG. 9 is a chart showing a simulated artery wall temperature profile at 15 GHz for 1 second wherein each line represents a layer and wherein layer 16, corresponding to 320 microns, indicates a peak temperature in the media and a temperature profile that saves endothelial cells and prevents thermal damage to cells of the adventitia.

The individual cell size selected for this particular display is 100 microns on a side (200 microns on a side in FIG. 8) and therefore provides an overview of a relatively large area for easy viewing of the overall effects throughout the simulated lesion volume. The entire field size is about 1800 microns on a side for FIG. 6 and FIG. 7, and 3600 microns for FIG. 8. In the isothermal segments of FIG. 6 and FIG. 7, the side in the x direction is 1800 microns wide and the side in the y direction is 900 microns. If desired, much smaller regions, such as the approximately, 30 micron depth of the endothelial, could be emphasized in greater detail to provide a picture of heating, in the endothelial, intimal, medial, or any other portion of the arterial wall. However, it will be noted that the larger scales are quite useful when an overview is desired. FIG. 9 is a printout that provide some relatively detailed feedback from the computer simulation regarding this region and any of about 50 different sections, as discussed hereinafter, although the focus of the simulation printout can be varied as desired.

Other graphs such as the temperature profile versus depth for various times during the heating period may be printed out. The plots may be in color. Additional information may be printed on each plot including values such as cell size, final temperature profile, type of antenna radiation, number of cubic millimeters at various selected temperature ranges, total energy in the cube after the power pulse, antenna radiated power, the number of computational cells illuminated, and so forth.

Comparing information regarding FIGS. 6, 7, and 8, the volume of material having a 10° C.–15° C. rise is greater for 40 GHz and less at both 95 GHz and 15 GHz. The time of the pulse in each case was 299 milliseconds. For short duration times of power application, the blood temperature at the surface of the lesion near the antenna rises with increasing frequency. The maximum temperature in the lesion moves to shallower depths with increasing frequency. Also the maximum temperature in the lesion increases with increasing frequency.

One basic premise shown from FIGS. 6, 7, and 8 is that heat contours can be significantly customized by frequency selection alone. Further customization is accomplished by selection of power level, duration of power delivery, and antenna type. The computer simulation can readily show the effects of such changes. The simulation results can be compared with information obtained from the test setup as discussed in the parent wherein temperature profiles, blood flow, type of vein, and so forth can be realistically determined, even prior to in vivo testing.

In a presently preferred embodiment of the simulation, a computational "myocardium" or heart tissue cube having a size that correlates to a region of tissue to be ablated is given the electrical and thermal characteristics of in-vivo myocardium. This selection is made for convenience and could be given the characteristics of plaque and encapsulating tissue. The characteristics can be specifically tailored for different areas of the cube or can be given average values. The cube or region or other shape selected as desired to be analyzed is subdivided into computational cells. In this simulation a cube of simulated myocardium is divided into 8000 small cubes with each cube being a computational cell.

The instantaneous heat of one arbitrary computational cell in the cube is given by:

$$Q_C = Q'_C + (\Delta Q_{RF} + \int \Delta Q_{HC}) \Delta t$$

where:

Q is the new heat energy in the computational cell;

$Q'_C$ is the previous heat energy level;

$\Delta Q_{RF}$ is the heat added due to absorption of microwave energy;

$\int \Delta Q_{HC}$ is the net heat added or lost by the cell from heat conduction; and $\Delta t$ is a small time increment.

The new temperature of the cell is given by:

$$T_C = Q_C/MS$$

where:

$T_C$ is the new cell temperature in °C.;

M is the mass of the cell; and

S is the specific heat of the cell.

Each cell is assumed to be a cube with six faces. The heat energy transferred through each face for one time increment is given by:

$$\Delta Q = -KA(\partial T/\partial r)\Delta t$$

where:

$\Delta Q$ is the heat transferred through one face;

K is the thermal conductivity of the cell;

$\partial T/\partial r$ is the temperature gradient from the center of one cube to the next: and A is the area of one face.

The electric field intensity in a cell is given by:

$$\hat{E}_i = \hat{E}_{01} \frac{e^{\gamma r_i}}{\gamma r_i^a}$$

where:

$\hat{E}$ is the electric field intensity resulting from the the radiation at the feed point of the antenna;

$\hat{E}_{01}$ is related to the relative magnitude and phase of radiation from the phase center of the antenna; and $$\gamma = \alpha + j\beta;$$

where:

$\alpha$ is the attenuation constant associated with the tissue;

$\beta$ is the phase shift constant, and $r_i$ is the distance from the antenna phase center to the center of a cell;

a=0 for a focused beam. 1 for a spreading beam in one dimension, and 2 for a spherically spreading beam.

Finally, the energy absorption at the cell is given by:

$$W_a = v\sigma|E|^2 \Delta t$$

where:

$W_a$ is the electromagnetic energy absorbed;

v is the volume of the cube, and $\sigma$ is the conductivity of the medium.

As discussed previously, the results from the simulation can be plotted in many ways to show the size and shape of the projected isothermal volumes. FIG. 9 shows a different presentation wherein the temperature vs. time is given for each of 50 layers of 20 micron thickness with each layer being represented by a separate line. Although any of the lines could be displayed individually, only lines 1–4, the top layers, and line 16, the hottest layer are clearly visible and are marked. Each line represents a thickness of 20 microns. The heating time is one second. The frequency is 15 GHz. The volume heated is 9.4 cubic millimeters. As can be seen from this graph, layer 16, would have been heated by about 16 degrees centigrade and is about 320 microns into the arterial wall which would probably typically be in the medial layer of the artery. It will be noted that the first one or two layers that Would be the endothelium would remain less than about 5 degrees centigrade, in this projection.

The program may also be altered to accept the desired heat contours as the input. By working backwards from a desired thermogenic profile, the program could be used to select the most appropriate choice of frequency, power level, duration of power delivery, antenna beamwidth from a particular selection of antennas, and other factors as discussed herein.

Figure 10:
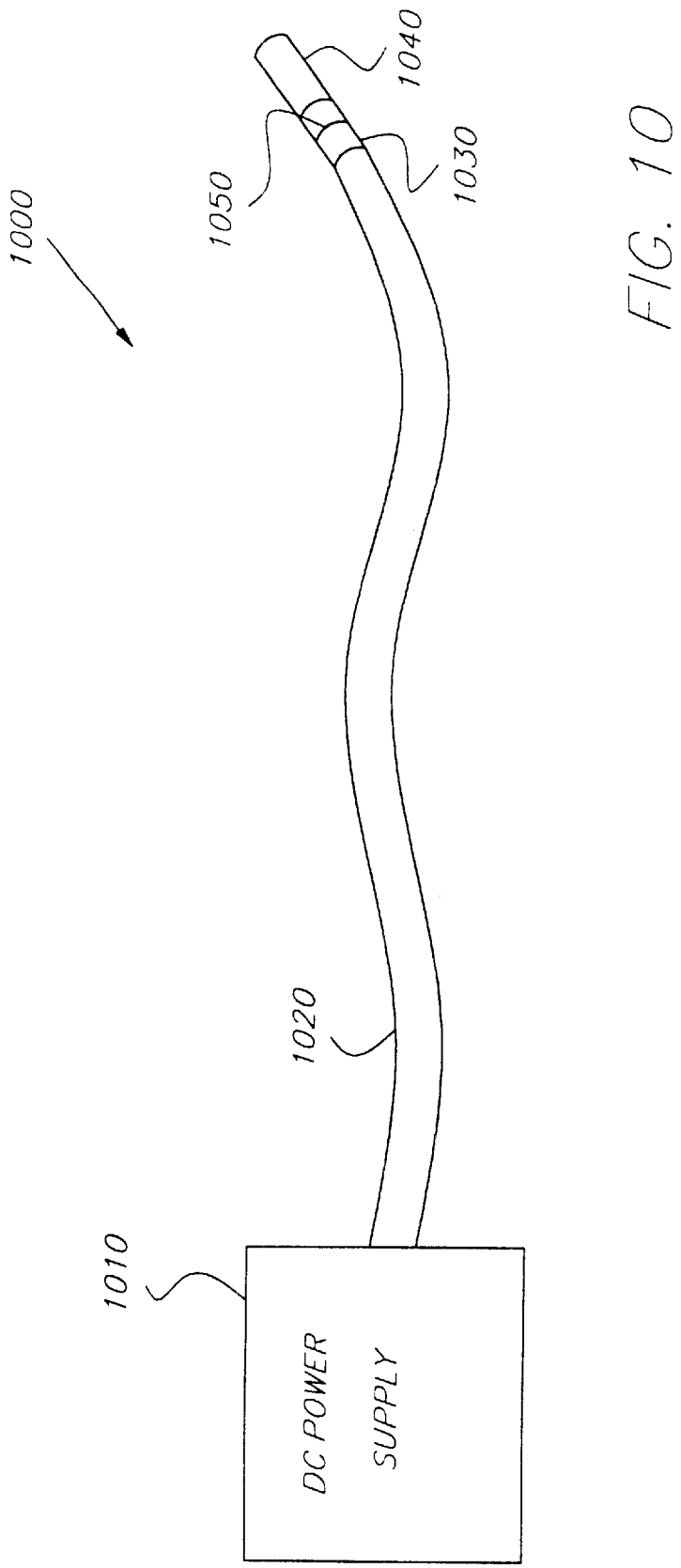
FIG. 10 is an schematical representation of another embodiment of the transcatheter of present invention using small chips for generation of the microwave signal.

FIG. 10 discloses oscillator chip catheter 1000 as another embodiment of the present invention. In this embodiment, a direct current power supply 1010 is used to supply power through catheter 1020 to one or more MIMIC chips 1030 that may use a radiating antenna 1040 such as a waveguide antenna, disk-loaded monopole antenna, or other antenna. The MMIC chips preferably reside in the catheter's distal end adjacent to the radiating element. Currently, MIMIC technology allows for cylindrical diameter dimensions of about 2.76 millimeters plus a thin sheath, which an excellent size that allows for convenient positioning of catheter 1020. The presently available chips cover the preferred range of frequencies, i.e., 2 GHz to 300 GHz, over a range from about 50 GHz to about 110 GHz. Chips operating in the lower frequencies of about 50 GHz presently offer more power per chip. To achieve greater than one watt of power delivered to radiating element 1040, if necessary, two or more, MMIC chips may be sequentially connect together. The chips may be physically connected with microstrip 1050.

Numerous variations and methods of operation may be used with the present invention. For instance, the catheter of the present invention may be used with other catheters and/or means to orient the catheter or may be built into other types of catheters. The present catheter may be modified to include simple orientation means. For instance, on the sheath side of the waveguide antenna, a simple resistivity sensor might be added that operates at a much lower frequency and with very low current but is directive and will sense the difference in resistivity of the arterial wall with or without an atheroma so as to quickly detect position and orient the device. Although the present device is preferably used instead of an angioplasty balloon, it has advantages that may also make it useful in combination with an angioplasty balloon, if desired, e.g., the ability to direct heat towards an asymmetrically positioned lesion. While the preferred embodiment antennas are disclosed in accord with the law requiring disclosure of the presently preferred embodiment of the invention, other types of antennas may also be used. Therefore, the foregoing disclosure and description of the invention are illustrative and explanatory thereof, and various changes in the method steps and also the details of the apparatus may be made within the scope of the appended claims, without departing from the spirit of the invention.

What is claimed is:

1. A method for treating atherosclerosis by controlling microwave radiation into an arterial wall having an endothelial layer for treating atherosclerosis, comprising:

providing a microwave conductor for a catheter;

adapting said microwave conductor for connection to a microwave power source;

providing a microwave antenna for said catheter; and limiting heating of the endothelial layer to a temperature rise that will not harm the endothelial layer while producing a temperature increase of over fifteen degrees Celsius in a selected portion of said arterial wall when utilizing continuous microwave radiation during a period of less than five seconds.

2. The method of claim 1, further comprising:

operating said microwave power source at a frequency in the range from 3 GHz to 300 GHz.

3. The method of claim 1, further comprising:

operating said microwave power source at a frequency in the range from 30 GHz to 300 GHz.

4. The method of claim 1, further comprising:

forming a transition member between a coaxial cable having inner and outer conductors to a waveguide having only an outer connector.

5. The method of claim 1, further comprising:

beveling a waveguide outer connector to form said antenna.

6. The method of claim 1, further comprising:

providing a monopole antenna.

7. The method of claim 1, further comprising:

providing a double disk loaded monopole antenna.

8. A computer simulated transcatheter method for treating atherosclerosis by controlling a radiation pattern into a simulated arterial wall having an atherosclerotic lesion therein, comprising:

determining energy added to computer cells that represent portions of said simulated arterial wall;

determining energy leaving said computer cells; and determining an isothermal profile within said arterial wall.

9. The computer simulated transcatheter method of claim 8, further comprising:

determining said isothermic profile for a time period within a desired time period range of less than five seconds.

10. The computer simulated transcatheter method of claim 8, further comprising:

determining said isothermic profile for a frequency within a desired frequency range of from 3 GHz to 300 GHz.

11. The computer simulated transcatheter method of claim 8, further comprising:

determining said isothermic profile for said atherosclerotic lesion given a size and location of said atherosclerotic lesion within said wall.

* * * * *

UNITED STATES PATENT AND TRADEMARK OFFICE
CERTIFICATE OF CORRECTION

PATENT NO.    : 6,496,736 B1                                     Page 1 of 1
DATED         : December 17, 2002
INVENTOR(S)   : James R. Carl It is certified that error appears in the above-identified patent and that said Letters Patent is hereby corrected as shown below:

<u>Title page,</u>
Item [75], Inventors, delete "Reginald Beer, Phillip D. Henry, and Antonio Pacifico"

Signed and Sealed this

Twenty-ninth Day of July, 2003

JAMES E. ROGAN
*Director of the United States Patent and Trademark Office*